United States Patent [19]
Friebe et al.

[11] Patent Number: 5,547,980
[45] Date of Patent: Aug. 20, 1996

[54] BICYCLIC SULFONES, PROCESSES FOR THEIR PRODUCTION AND PHARMACEUTICAL AGENTS CONTAINING THEM

[75] Inventors: Walter–Gunar Friebe; Erhard Reinholz, both of Mannheim; Henning Wilhelms, Weinheim, all of Germany

[73] Assignee: Boehringer Mannheim GmbH, Mannheim, Germany

[21] Appl. No.: 199,249

[22] PCT Filed: Aug. 26, 1992

[86] PCT No.: PCT/EP92/01960

§ 371 Date: Feb. 28, 1994

§ 102(e) Date: Feb. 28, 1994

[87] PCT Pub. No.: WO93/05034

PCT Pub. Date: Mar. 18, 1993

[30] Foreign Application Priority Data

Aug. 29, 1991 [DE] Germany .......................... 41 28 690.1

[51] Int. Cl.$^6$ ........................ A61K 31/38; C07D 333/52
[52] U.S. Cl. ................................. 514/443; 549/53
[58] Field of Search ................... 549/57, 55, 53, 549/439, 28, 23; 514/443

[56] References Cited

U.S. PATENT DOCUMENTS

| | | | |
|---|---|---|---|
| 2,666,762 | 1/1954 | Cusic | 549/53 |
| 2,876,235 | 3/1959 | Voegtli | 549/57 |
| 3,070,606 | 12/1962 | Anderson | 549/53 |
| 3,547,931 | 12/1970 | Kaiser et al. | 549/53 |
| 3,549,656 | 12/1970 | Petersen et al. | 549/57 |
| 3,629,267 | 12/1971 | Kaiser et al. | 549/57 |
| 3,910,955 | 10/1975 | Chapman et al. | 549/57 |
| 4,352,808 | 10/1982 | Rane et al. | 424/258 |
| 4,654,352 | 3/1987 | Ray | 514/324 |
| 4,801,605 | 1/1989 | Hutchison | 514/432 |
| 5,240,927 | 8/1993 | Hrib et al. | 549/57 |

Primary Examiner—José G. Dees
Assistant Examiner—Deborah Lambkin
Attorney, Agent, or Firm—Nikaido, Marmelstein, Murray & Oram LLP

[57] ABSTRACT

Bicyclic sulfones of the formula I in which

Y is a halogen atom,

Z is a halogen atom or hydrogen, m and n, that are different and represent an integer 0 or 1, A and B each represent hydrogen or together represent a valency bond, $X_1$ and $X_2$ each represent $NR_1R_2$ or, if A and B represent a valency bond, one of the two residues $X_1$ or $X_2$ represents hydrogen and the other represents $NR_1R_2$, $R_1$ denotes a $C_1$–$C_6$ alkyl, $C_3$–$C_7$ cycloalkyl, $C_2$–$C_6$ alkenyl or a benzyl residue substituted if desired, by halogen, $C_1$–$C_6$ alkyl, $C_1$–$C_6$ alkoxy or hydroxy and $R_2$ denotes hydrogen or a residue from the definition of $R_1$ or $R_1$ and $R_2$ together with the nitrogen atom form a heterocyclic ring which if desired, contains further heteroatoms and/or can be substituted by $C_1$–$C_6$ alkyl, $C_1$–$C_6$ alkoxy, $C_1$–$C_6$ alkanoyl or benzhydryl, their tautomers, enantiomers, diastereomers and physiologically tolerated salts, processes for their production and pharmaceutical agents which contain these compounds for the treatment of allergic diseases as well as bronchospastic and bronchoconstrictory reactions caused by inflammation.

9 Claims, No Drawings

BICYCLIC SULFONES, PROCESSES FOR THEIR PRODUCTION AND PHARMACEUTICAL AGENTS CONTAINING THEM

The present invention concerns bicyclic sulfones, processes for their production and pharmaceutical agents which contain these compounds.

The invention concerns bicyclic sulfones having the general formula I

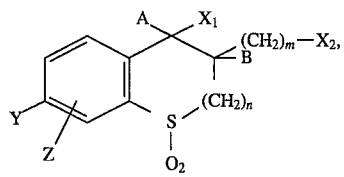

in which
Y is a halogen atom,
Z is a halogen atom or hydrogen,
m and n, that are different and represent an integer 0 or 1,
A and B each represent hydrogen or together represent a valency bond,
$X_1$ and $X_2$ each represent $NR_1R_2$ or, if A and B represent a valency bond, one of the two residues $X_1$ or $X_2$ represents hydrogen and the other represents $NR_1R_2$,
$R_1$ denotes a $C_1$–$C_6$ alkyl, $C_3$–$C_7$ cycloalkyl, $C_2$–$C_6$ alkenyl or a benzyl residue substituted if desired, by halogen, $C_1$–$C_6$ alkyl, $C_1$–$C_6$ alkoxy or hydroxy
$R_2$ denotes hydrogen or a residue from the definition of $R_1$ or
$R_1$ and $R_2$ together with the nitrogen atom form a heterocyclic ring which if desired, contains further heteroatoms and/or can be substituted by $C_1$–$C_6$ alkyl, $C_1$–$C_6$ alkoxy, $C_1$–$C_6$ alkanoyl or benzhydryl,
their tautomers, enantiomers, diastereomers and physiologically tolerated salts.

The novel compounds of the general formula I have valuable pharmacological properties, in particular they can inhibit antigen-induced contraction of lung tissue strips. They are therefore suitable for the treatment of allergic diseases as well as of bronchospastic and bronchoconstrictory reactions due to inflammation.

The alkyl residues in the said groups can be straight-chained or branched. Preferred alkyl residues are the methyl, ethyl, n-propyl, isopropyl, n-butyl, isobutyl, tert.-butyl, n-pentyl and 3-pentyl residue.

Alkoxy preferably denotes methoxy or ethoxy. An alkenyl residue is preferably allyl.

Halogen atoms are in particular fluorine, chlorine and bromine.

Cycloalkyl residues preferably denote cyclopropyl, cyclobutyl, cyclopentyl, cyclohexyl or cycloheptyl, in particular cylcopentyl.

Heterocyclic rings are for example pyrrolidine, piperidine, morpholine, thiomorpholine, piperazine and homopiperidine.

Apart from the compounds mentioned in the examples, the invention in particular relates to all substances which have any possible combination of the substituents mentioned in the examples.

The process according to the invention for the production of the compounds of formula I is characterized in that a compound of the general formula II

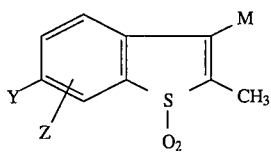

in which Y and Z have the stated meaning and M represents a reactive residue, is reacted in a known manner with a compound of the general formula III $$HNR_1R_2 \qquad (III),$$

in which $R_1$ and $R_2$ have the stated meaning,
and subsequently, if desired, the compounds of formula I that are obtained are converted into their salts by reaction with physiologically tolerated acids.

Clorine and bromine come into consideration as the reactive residues M.

It is expedient to react compounds of formula II with compounds of formula III in a solvent such as for example a lower alcohol such as methanol, ethanol or isopropanol or an ether such as tetrahydrofuran or an amine such as pyridine. However, is it also possible to use excess components of formula III as the solvent.

The starting compounds II and III are substances known in the literature or can be produced in analogy to processes known in the literature. The synthesis of 3,6-dichloro-2-methyl-benzo[b]thiophene-1,1-dioxide is described in J. Heterocycl. Chem. 3, 174 (1966).

Product mixtures are formed under the respective reaction conditions the processing of which yields either two different products or only one main product. The products obtained are unequivocally characterized by physical data (melting point, IR and NMR data).

Salts which come into consideration as pharmacologically tolerated salts are those of non-toxic, inorganic or organic acids such as e.g. hydrochloric acid, sulphuric acid, phosphoric acid, hydrobromic acid, acetic acid, lactic acid, citric acid, malic acid, benzoic acid, salicylic acid, malonic acid, maleic acid, succinic acid or diaminocaproic acid.

The salts are obtained in the usual manner e.g. by neutralizing compounds of formula I with the corresponding acids.

For the production of pharmaceutical agents, the compounds of the general formula I are mixed in a known manner with suitable pharmaceutical vehicles, aromatic substances, flavourings and dyes and are for example formed into tablets or coated tablets or suspended or dissolved in water or in an oil such as olive oil with addition of appropriate auxiliary substances.

The substances of the general formula I can be administered orally and parenterally in a liquid or solid form. Water is preferably used as the injection medium which contains the usual stabilizers, solubilizers and/or buffers for injection solutions. Such additives are for example tartrate or borate buffer, ethanol, dimethylsulfoxide, complexing agents (such as ethylenediaminetetraacetic acid), high molecular polymers (such as liquid polyethylene oxide) to regulate the viscosity or polyethylene derivatives of sorbitol anhydrides. Solid vehicles are for example starch, lactose, mannitol, methyl cellulose, talcum, highly dispersed silicic acid, high molecular polymers (such as polyethylene glycols).

Suitable formulations for oral administration can, if desired, contain flavourings and sweeteners. For an external application, the substances I according to the invention can be used in the form of powders and ointments. For this they are for example mixed with physiologically tolerated diluents or common ointment bases in powder form.

The administered dose depends on the age, health and weight of the recipient, the extent of the disease, the type of other treatments which may be being carried out at the same time, the frequency of the treatments and the type of desired effect. The daily dose of the active compound is usually 0.1 to 50 mg/kg body weight. Normally 0.5 to 40 and preferably 1.0 to 20 mg/kg/day in one or several applications per day are effective in order to obtain the desired results.

Apart from the substances mentioned in the examples, the following compounds are preferred within the sense of the present invention:
1. 6-chloro-2-(4-thiomorpholino-methyl)benzo[b]thiophene-1,1-dioxide
2. 6-chloro-2-(N-butylamino-methyl)benzo[b]thiophene-1,1-dioxide
3. 6-chloro-2-(N-cyclopentylamino-methyl)benzo[b]thiophene1,1-dioxide
4. 6-chloro-2-(N-methylamino-methyl)benzo[b]thiophene-1,1 dioxide
5. 6-chloro-2-methyl-3-diethylamino-benzo[b]thiophene-1,1 dioxide
6. 6-chloro-2-methyl-3-pyrrolidino-benzo[b]thiophene-1,1 dioxide
7. 6-chloro-2-methyl-3-dimethylamino-benzo[b]thiophene-1,1 dioxide
8. 6-chloro-2-methyl-3-piperidino-benzo[b]thiophene-1,1 dioxide
9. 6-chloro-2-methyl-3-(4-methoxy-piperidino)benzo[b]thiophene-1,1-dioxide
10. 6-chloro-2-methyl-3-hexamethylenimino-benzo[b]thiophene-1,1-dioxide
11. 6-chloro-2-methyl-3-(4-thiomorpholino)benzo[b]thiophene-1,1-dioxide
12. 6-chloro-2-methyl-3-N,N-diallylamino-benzo[b]thiophene-1,1-dioxide

EXAMPLE 1

6-chloro-2-(N,N-diethylamino-methyl)benzo[b]thiophene-1,1 dioxide

A mixture of 37.3 g (0.15 mol) 3,6-dichloro-2-methyl-benzo[b]thiophene-1,1-dioxide, 200 ml methanol and 45 ml diethylamine is heated for 4 hours to reflux. Afterwards it is concentrated by evaporation, taken up in ethyl acetate, washed with water, dried, concentrated and chromatographed on silica gel (eluting agent ethyl acetate/isohexane 1:1). 29.5 g of the title compound (62% of the theoretical yield) having a melting point of 58°–59° C. is isolated.

The hydrochloride with a melting point of 217°–218° C. is obtained by adding excess ethereal hydrogen chloride solution to the ethyl acetate solution.

EXAMPLE 2

6-chloro-2-(4-morpholino-methyl)benzo[b]thiophene-1,1-dioxide and 6-chloro-2-methyl-3-(4-morpholino)benzo[b]thiophene-1,1-dioxide A mixture of 5.0 g (20 mmol) 3,6-dichloro-2-methylbenzo[b]thiophene-1,1-dioxide, 40 ml methanol and 6.5 ml morpholine is heated for 24 h to reflux. Afterwards it is concentrated by evaporation and chromatographed on silica gel (eluting agent ethyl acetate/isohexane 1:1). 1.4 g 6-chloro-2-methyl-3-(4-morpholino)benzo[b]thiophene-1,1-dioxide (23% of the theoretical yield) of melting point 220°–222° C. is obtained as the first fraction and 1.6 g 6-chloro-2-(4-morpholino-methyl)benzo[b]thiophene-1,1-dioxide (27% of the theoretical yield) of melting point 127°–129° C. as the second fraction.

EXAMPLE 3

The following are isolated in an analogous manner to that described in example 1 or 2 from the product mixture of the reaction of 3,6-dichloro-2-methyl-benzo[b]thiophene-1,1-dioxide and the respective amine:

| Name | Yield % | Melting point °C. (solvent) |
| --- | --- | --- |
| a) 7-chloro-3,4-bis-pyrrolidino-benzo[b]thian-1,1-dioxide from pyrrolidine | 15 | 70–71 (isohexane) |
| b) 6-chloro-2-pyrrolidinomethyl-benzo[b]thiophene-1,1-dioxide from pyrrolidine | 37 | 192–194 (ethanol) |
| c) 6-chloro-2-dimethylamino-methyl-benzo[b]thiophene-1,1-dioxide from dimethylamine | 21 | 173–174 (ethyl acetate) |
| d) 7-chloro-3,4-bis-methylamino-benzo[bl9 thian-1,1-dioxide dihydrochloride from methylamine | 36 | 216–218 (acetone) |

EXAMPLE 4

6-chloro-2-piperidinomethyl-benzo[b]thiophene-1,1-dioxide

A mixture of 3.75 g 3,6-dichloro-2-methyl-benzo[b]-thiophene-1,1-dioxide and 35 ml piperidine is stirred for 4 hours at 80° C., water is subsequently added and it is extracted with ethyl acetate. The extract is concentrated by evaporation and it is ground with ethyl acetate. 1.6 g of the title compound (36% of the theoretical yield) of melting point 154°–156° C. is isolated.

EXAMPLE 5

The following are isolated in an analogous manner to that described in example 4 from the product mixture of the reaction of 3,6-dichloro-2-methyl-benzo[b]thiophene-1,1-dioxide and the respective amine, if desired, after chromatographic separation:

| Name | Yield % | Melting point °C. (solvent) |
| --- | --- | --- |
| a) 6-chloro-2-(4-methoxy-piperidnomethyl)benzo[b]thiophene-1,1-dioxide from 4-methoxy-piperidine | 37 | 150–152 (ethyl acetate) |
| b) 6-chloro-2-(4-methyl-piperidinomethyl)benzo[b]thiophene-1,1-dioxide from 4-methyl-piperidine | 42 | 202–203 (ethyl acetate) |
| c) 6-chloro-2-methyl-3-(4-methyl piperidino)benzo[b]thiophene-1,1-dioxide from 4-methyl-piperidine | 13 | 120–122 (isohexane) |
| d) 7-chloro-3,4-bis-(4-methyl-piperidino)benzo[b]thian-1,1-dioxide from 4-methyl-piperidine | 26 | 94–96 (isohexane) |
| e) 6-chloro-2-hexamethylen-iminomethyl-benzo[b]thiophene 1,1-dioxide from hexamethylenimine | 49 | 103–104 (2-propanol) |
| f) 6-chloro-2-(4-methyl-piper-azinomethyl)benzo[b]thiophene-1,1-dioxide from N-methyl-piperazine | 34 | 182–183 (ethyl acetate) |
| g) 6-chloro-2-(4-acetyl-piper-azinomethyl)benzo[b]thio- | 26 | 135–136 (ether) |

-continued

| Name | Yield % | Melting point °C. (solvent) |
|---|---|---|
| phene-1,1-dioxide from N-acetyl-piperazine | | |
| h) 6-chloro-2-(4-diphenylmethyl-piperazinomethyl)benzo[b]-thiophene-1,1-dioxide from 1-benzhydryl-piperazine | 63 | 221–222 (acetone) |
| i) 6-chloro-2-(N,N-diallylamino-methyl)benzo[b]thiophene-1,1-dioxide from diallylamine | 55 | 61–62 (isohexane) |
| j) 6-chloro-2-[N-cyclopentyl-N-(3-methoxybenzyl)aminomethyl] benzo[b]thiophene-1,1-dioxide hydrochloride from N-cyclopentyl-N-(3-methoxy-benzyl)amine | 29 | 208–210 (acetone) |
| k) 7-chloro-3,4-bis-thiomorpho-lino-benzo[b]thian-1,1-dioxide from thiomorpholine | 27 | 165–167 (ether) |
| l) 7-chloro-3,4-bis-n-butyl-amino-benzo[b]thian-1,1-dioxide-dihydrochloride from n-butylamine | 34 | 148–150 (ether) |
| m) 7-chloro-3,4-bis-cyclopentyl-amino-benzo[b]thian-1,1-dioxide-dihydrochloride from cyclopentylamine | 21 | 196–198 (ether) |

EXAMPLE 6

5,6-dichloro-2-(N,N-diethylamino-methyl)benzo[b]-thiophene- 1,1-dioxide-hydrochloride The title compound is obtained in 22% yield as a hydrochloride of melting point 247°–248° C. (from ethyl acetate) in an analogous manner to that described in example 1 from 3,5,6-trichloro-2-methyl-benzo[b]thiophene-1,1-dioxide and diethylamine.

EXAMPLE 7

6,7-dichloro-2-(N,N-diethylamino-methyl)benzo[b] thiophene- 1,1-dioxide-hydrochloride The title compound is obtained in 19% yield as a hydrochloride of melting point 216°–218° C. (from ethyl acetate) in an analogous manner to that described in example 1 from 3,6,7-trichloro-2-methyl-benzo[b]thiophene-1,1-dioxide and diethylamine.

The trichloro-methyl-benzo[b]thiophene-1,1-dioxides used as starting materials for example 6 and 7 can be obtained as follows:

10.0 g (0.05 mol) 3,4-dichloro-propiophenone is added in portions to 24 ml chlorosulfonic acid, it is stirred for 3 hours at 100° C., poured onto ice, filtered, the precipitate is stirred out with 50 ml concentrated ammonia, filtered, washed with water and the residue is chromatographed on silica gel (eluting agent isohexane/ethyl acetate 9:1). 6.8 g 3,5,6-trichloro-2-methyl-benzo[b]thiophene-1,1-dioxide (48% of the theoretical yield) of melting point 194°–196° C. as well as 2.9 g 3,6,7-trichloro-2-methyl-benzo[b]thiophene-1,1-dioxide (20% of the theoretical yield) of melting point 179°–181° C. are isolated.

TEST REPORT

Inhibition of the antigen-induced constriction of passively sensitized guinea-pig - lung parenchymal - strips in vitro (organ bath)

For the in vitro examination of the compounds according to the invention, the inhibition of the antigen-induced constriction of passively sensitized guinea-pig lung parenchymal strips was measured as described in the following:

Pirbright-White guinea-pigs were stunned by a blow on the neck and exsanguinated. The lungs were rinsed substantially free of blood in situ using Krebs buffer, pH 7.4. Subsequently the lung was excised, cut into strips (ca. 20×4×4 mm) and the strips were passively sensitized for one hour at room temperature with a 1:50 dilution of a homologous anti-ovalbumin antiserum and then washed once with Krebs buffer. The antiserum had previously been produced in guinea-pigs of the same strain according to DAVIES (1) by repeated injection of ovalbumin (2×crystallized) with addition of complete Freund's adjuvant. The antiserum was stored undiluted at −18° C. until use. Subsequently the lung strips were suspended individually in 10 ml water baths on an isometric measuring recorder with an initial tension of 1.2 g. Afterwards the baths were filled with Krebs buffer and gassed continuously at 37° C. with $O_2$ (95%) and $CO_2$ (5%). The constrictions of the lung strips were recorded via an amplifier on a recorder. After a 30 minute adaptation phase, histamine control spasms were generated to detect the responsiveness of the pieces of organ, they were washed, subsequently preincubated for 20 minutes at 37° C. with the test substance and afterwards the ovalbumin-induced constriction was triggered. The inhibitory effects of the compounds according to the invention were expressed as percentage reduction of the constriction amplitudes of the "samples with test substance" in relation to the "untreated control constrictions".

(1) DAVIES, G. E., T. P. Johnstone

Quantitative studies on anaphylaxis in guinea-pigs passively sensitized with homologous antibody. Inter. Arch. Allergy 41, 648-454 (1971)

TABLE

% inhibition of the ovalbumin (0.1 µg/ml) induced constriction of passively sensitized lung parenchymal strips (guinea-pig)
20 min/37° C. preincubation time (organ bath technique)

| Substance example No. | Concentration (20 µg/ml) | n |
|---|---|---|
| aminophylline | 26* | 6 |
| 1 | 53 | 2 |
| 3a) | 25 | 3 |
| 6 | 51 | 3 |
| 7 | 88 | 3 |
| 5 l) | 25 | 3 | n = number of tests
* = 200 µg/ml

We claim:
1. A bicyclic sulfone of the formula

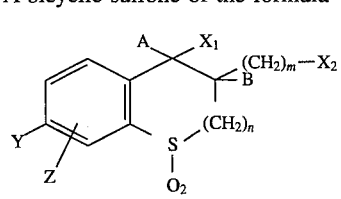

(I)

wherein

Y is halogen;

Z is halogen or hydrogen;

m is an integer 1;

n is an integer 0;

A and B together are a valency bond;

$X_1$ is hydrogen and $X_2$ is $-NR_1R_2$;

$R_1$ is a member selected from the group consisting of $C_1$–$C_6$ alkyl, $C_3$–$C_7$ cycloalkyl, $C_2$–$C_6$ alkenyl and benzyl, with said benzyl being unsubstituted or substituted by halogen, $C_1$–$C_6$ alkyl, $C_1$–$C_6$ alkoxy or hydroxy; and $R_2$ is hydrogen or a member as defined for $R_1$ or a tautomer, enantiomer, diastereomer or physiologically acceptable salt thereof.

2. Sulfone of claim 1, wherein the sulfone is 6,7-dichloro-2-(N,N-diethylamino-methyl)benzo[b]thiophene-1,1-dioxi-dehydrochloride.

3. Sulfone of claim 1, wherein the sulfone is selected from the group consisting of
   a) 6-chloro-2-(N-butylamino-methyl)benzo[b]thiophene-1,1-dioxide
   b) 6-chloro-2-(N-cyclopentylamino-methyl)benzo[b]thiophene- 1,1-dioxide and
   c) 6-chloro-2-(N-methylamino-methyl)benzo[b]thiophene-1,1 dioxide.

4. Sulfone of claim 1, wherein the sulfone is selected from the group consisting of
   a) 6-chloro-2-(N,N-diethylamino-methyl)benzo[b]thiophene-1,1 dioxide and
   b) 6-chloro-2-dimethylamino-methyl-benzo[b]thiophene-1,1-dioxide.

5. Sulfone of claim 1, wherein the sulfone is selected from the group consisting of
   a) 6-chloro-2-(N,N-diallylaminomethyl)benzo[b]thiophene-1,1-dioxide
   b) 6-chloro-2-[N-cyclopentyl-N-(3-methoxybenzyl) aminomethyl]benzo[b]thiophene-1,1-dioxide hydrochloride and
   c) 5,6-dichloro-2- (N,N-diethylamino-methyl)benzo[b]-thiophene-1,1-dioxide-hydrochloride.

6. A process for producing a sulfone of claim 1, comprising reacting a compound of the formula

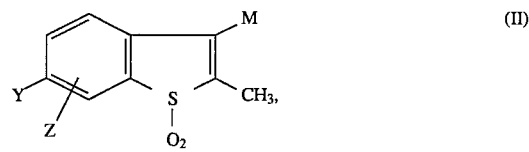 (II)

wherein y and z are defined in claim 1 and M is a reactive residue, with a compound of the formula

HNR$_1$R$_2$ (III)

wherein $R_1$ and $R_2$ are defined in claim 1.

7. Pharmaceutical composition suitable for the treatment of allergic diseases or bronchospastic or bronchoconstrictory reactions caused by inflammation, comprising an effective amount of compound of claim 1 and a pharmaceutically acceptable carrier therefor.

8. A method of treating an allergic disease in a patient in need of such treatment, said method comprising administering to said patient an antiallergy-effective amount of a sulfone of claim 1.

9. A method of treating bronchospastic and/or bronchoconstrictory reactions caused by inflammation in a patient in need of such treatment, said method comprising administering to said patient an antibronchospastic or antibronchoconstrictory-effective amount of a sulfone of claim 1.

* * * * *